United States Patent [19]

Shim

[11] 4,288,628
[45] Sep. 8, 1981

[54] PROCESS FOR THE PRODUCTION OF MONO-HALOTHIOPHENOLS AND THIOPHENOLS

[75] Inventor: Kyung S. Shim, Irvington, N.Y.

[73] Assignee: Stauffer Chemical Company, Westport, Conn.

[21] Appl. No.: 18,708

[22] Filed: Mar. 8, 1979

[51] Int. Cl.$^3$ ............... C07C 149/34; C07C 149/28
[52] U.S. Cl. .................................. 568/65; 568/67
[58] Field of Search ............... 260/609 D; 568/65, 67

[56] References Cited

U.S. PATENT DOCUMENTS

| | | | |
|---|---|---|---|
| 1,706,489 | 3/1929 | Hoffa et al. | 260/609 |
| 1,825,662 | 10/1931 | Hale | 260/609 |
| 2,438,838 | 3/1948 | Ballard et al. | 260/609 |
| 2,443,811 | 6/1948 | Winkler et al. | 260/609 |
| 2,467,222 | 4/1949 | Pavlic | 260/609 |
| 2,490,257 | 12/1949 | Crowley et al. | 260/609 D |
| 2,506,416 | 5/1950 | Gilbert et al. | 260/609 |
| 2,792,422 | 5/1957 | Harris et al. | 260/609 |
| 2,922,820 | 1/1960 | Rocklin | 260/609 |
| 2,947,788 | 8/1960 | Pitt | 260/608 |
| 3,326,981 | 6/1967 | Levy et al. | 260/609 |
| 3,331,205 | 7/1967 | Laufer | 260/609 |
| 3,374,274 | 3/1968 | Spainhour | 260/609 |
| 3,734,969 | 5/1973 | Pitt | 260/609 D |
| 3,799,989 | 3/1974 | Sherk et al. | 260/609 D |
| 3,883,599 | 5/1975 | Mariotti et al. | 260/609 D |
| 4,006,186 | 1/1977 | Engels et al. | 260/609 D |
| 4,024,191 | 5/1977 | Scoggin | 260/609 D |

FOREIGN PATENT DOCUMENTS

| | | | |
|---|---|---|---|
| 45-19046 | 6/1970 | Japan | 260/609 D |
| 46-8293 | 3/1971 | Japan | 260/609 D |

*Primary Examiner*—Donald G. Daus
*Assistant Examiner*—M. C. Eakin
*Attorney, Agent, or Firm*—William C. Gerstenzang

[57] ABSTRACT

A process for the production of a mono-halothiophenol, e.g. para-chlorothiophenol, and thiophenol. The process comprises reacting a reactant mixture of benzene and dihalobenzene, e.g. para-dichlorobenzene, with hydrogen sulfide in the presence of an absorptive catalyst, such as activated carbon, calcined petroleum coke, etc.

16 Claims, 1 Drawing Figure

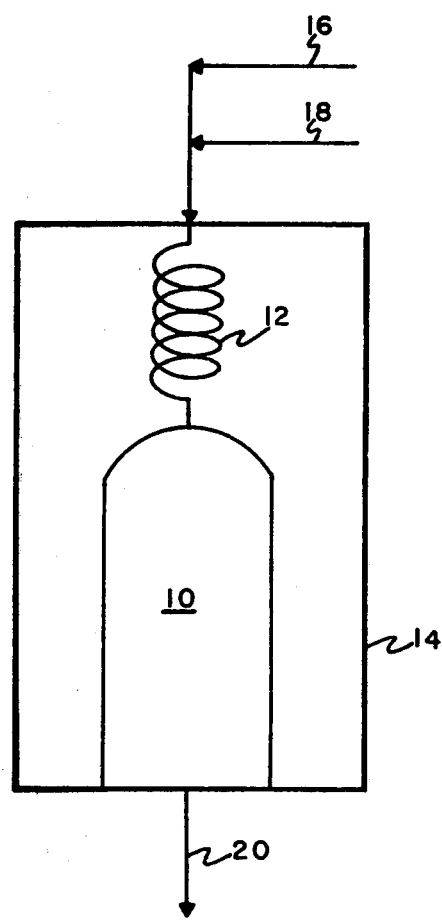
FIGURE I.

4,288,628

PROCESS FOR THE PRODUCTION OF MONO-HALOTHIOPHENOLS AND THIOPHENOLS

CROSS-REFERENCE TO RELATED APPLICATION

This application is related to U.S. Application Ser. No. 802,682, filed on June 2, 1977, corresponding to Belgian Pat. No. 867,645, granted on Nov. 30, 1978, to Shim and Skrzec, assigned to the assignee of this application, which describes producing thiophenol by reacting benzene with hydrogen sulfide in contact with an absorptive catalyst.

BACKGROUND OF THE INVENTION

1. Field of the Invention

This invention relates to a process for the production of mono-halothiophenol and thiophenol.

Mono-halothiophenols, in particular, chlorothiophenols, are useful intermediates in the manufacture of dyes and insecticides. In particular, para-chlorothiophenol has become an important commercial chemical, its principle current use being as an intermediate in the synthesis of pesticides.

Thiophenols are useful as additives to lubricating oils, as intermediates in organic synthesis, as insecticides, fungicides and parasiticides and as ingredients of insecticidal, fungicidal and parasiticidal compositions, and are useful in the preparation of synthetic resins, rubber, vulcanization accelerators, and the like.

2. Prior Art

U.S. Pat. No. 2,490,257 to Crowley et al. describes the production of thiophenols by a vapor phase reaction of chlorobenzene and hydrogen sulfide in the presence of a catalyst, such as wood charcoal or alumina. Yields, are, however, low.

Japanese Pat. No. 1970-19046 describes the production of thiophenols by a vapor phase reaction of chloro or bromobenzene with hydrogen sulfide in the presence of a catalyst of a sulfide of Cu, Ag, Zn, Cd, Pb, Bi, Co, or Mo supported on activated carbon.

U.S. Pat. No. 3,799,989 to Sherk et al. describes the production of thiophenols at increased yields by the vapor phase reaction of chlorobenzene and hydrogen sulfide in a reactor containing a noncatalytic filler and with recycling of certain byproducts.

Japanese Pat. No. 1971-8293 describes the production of thiophenols by the vapor phase reaction of chlorobenzene and hydrogen sulfide in the presence of a catalyst, such as activated charcoal or alumina, and with recycling of certain byproducts.

The entire disclosures of all of the aforementioned references, including the Related Application, are incorporated herein by reference.

Para-chlorothiophenol is typically made from chlorobenzene by chlorosulfonation, followed by metal acid reduction. Unfortunately, such a process is too costly to yield a low priced para-chlorothiophenol.

The aforementioned Crowley et al. reference indicates that the reaction of para-dichlorobenzene with hydrogen sulfide in the presence of charcoal produces para-dithiophenol (col. 4, l. 65). The aforementioned Sherk et al. reference also implies that all the halo substituents on the aromatic ring will be replaced by —SH when a dihalobenzene is reacted with hydrogen sulfide. The reference further indicates that benzene is normally a major byproduct from the reaction of chlorobenzene with hydrogen sulfide (col. 1, l. 28-51).

SUMMARY OF THE INVENTION

Accordingly, it is an object of the present invention to provide a process for producing thiophenol from benzene and hydrogen sulfide at increased yields and, to simultaneously produce a mono-halothiophenol, particularly para-chlorothiophenol.

Other objects and advantages will become apparent from the following description.

According to the present invention, a reactant mixture of benzene and a dihalobenzene is reacted with hydrogen sulfide in the presence of an absorptive catalyst to produce a mixture of mono-halothiophenol and thiophenol. It has unexpectedly been found that increased yields of thiophenol are produced while simultaneously producing mono-halothiophenols.

BRIEF DESCRIPTION OF THE DRAWING

FIG. 1 is a diagrammatic representation of an embodiment of an apparatus used in the process of this invention.

DETAILED DESCRIPTION OF THE INVENTION

It is believed that the process of this invention proceeds according to the following formula:

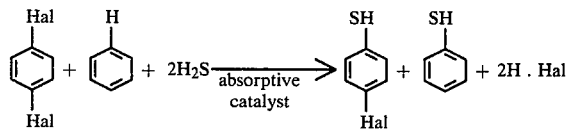

wherein "Hal" is halogen, preferably, chlorine.

The preferred dihalobenzene is para-dichlorobenzene. When the preferred reactant mixture of benzene and para-dichlorobenzene is reacted with hydrogen sulfide in the presence of the absorptive catalyst, a mixture of para-chlorothiophenol and thiophenol is produced.

It has unexpectedly been found that dihalobenzene acts somewhat as a catalyst for the reaction of benzene with hydrogen sulfide causing the production of substantially greater yields of thiophenol than that which would be produced in the absence of dihalobenzene. These greater yields of thiophenol are produced even though substantial yields of mono-halothiophenol are produced. One skilled in the art would expect that the reaction of hydrogen sulfide with dihalobenzene would be preferred, thus producing low yields of thiophenol. One would also expect that both of the halo substituents on the dihalobenzene would react with hydrogen sulfide to produce dithiophenol. It has been found however that high yields of thiophenol are produced while simultaneously producing mono-halothiophenol.

The absorptive catalyst used is a material having a large surface area, in the order of about 1 to about 1,000 square meters per gram. Suitable catalysts include active carbons, petroleum coke, various charcoals, calcined petroleum cokes, alumina, clay, silica gel, molecular sieves and various mixtures thereof. Optionally, the absorptive catalysts can be admixed with, or impregnated with, co-catalysts such as zinc sulfide, cobalt sulfide, cadmium sulfide, and other transition metal sulfides. Furthermore, various combinations of the aforementioned types of catalysts can be employed, such as mixtures of impregnated catalysts with non-impregnated catalysts, etc. The preferred catalysts are the charcoal and zinc sulfide impregnated charcoals.

The absorptive catalyst may be a solid substance which has an active surface due to its chemical nature and/or to its degree of subdivision or amounts of available reaction surface. The absorptive catalyst may be in the form of a fine powder, in the form of pellets or other formed pieces of suitable size. A single catalyst or mixtures of different catalysts may be employed and may be used with or without promotors and/or active or inert supports, such as pumice, silica gel, activated charcoal, kieselguhr, etc.

The catalysts and co-catalysts that may be utilized in the process of this invention are well known to those skilled in the art, see for example, the aforementioned Belgian Pat. No. 802,682, Crowley et al. and Japanese Pat. Nos. 1970-19046 and 1971-8293.

The hydrogen sulfide and reactant mixture of benzene and dihalobenzene may be passed over the catalyst at any convenient rate, depending upon equipment utilized, temperature, pressure, reactant mixture and the products desired. A feed rate of reactant mixture and hydrogen sulfide of from about 1 to about 80 moles per liter of catalyst per hour will generally produce suitable results, although higher or lower rates may be used. A preferred range of feed rate is from about 5 to about 15 moles per liter of catalyst per hour.

The reaction may be allowed to take place for any suitable length of time. The duration of the run will depend upon feed rate, the reaction mixture utilized, temperature, pressure and products desired. Durations of from about 5 to about 60 seconds are generally suitable although longer or shorter runs may be desirable in some cases.

The hydrogen sulfide, benzene and dihalobenzene may be reacted in any proportions, but for the sake of efficiency, it is preferred to use a molar excess of hydrogen sulfide. A mole ratio of hydrogen sulfide to reactant mixture of about 1:1 to about 10:1 will produce satisfactory results, although higher or lower mole ratios may be used if desired. Mole ratios greater than 2:1 are preferred, with about 4:1 to about 8:1 having been found effective in producing substantial yields of thiophenols and monohalothiophenols.

The mole ratio of benzene to dihalobenzene is not critical. It is preferred, however, to have present an amount of dihalobenzene which produces an increase in yield of thiophenol over that which would be produced without the dihalobenzene present. A preferred mole ratio of benzene to dihalobenzene is from about 0.5:1 to about 3:1.

Reaction temperatures of from about 400° C. to about 900° C. may be utilized, preferably from about 400° C. to about 600° C.

The reaction may also be carried out under pressure, for example, 100 psig and higher, although for economic reasons atmospheric pressure is preferred.

The products of reaction, e.g. p-chlorothiophenol, thiophenol, byproducts and unreacted reaction mixture, can be recovered after one pass through an absorptive catalyst or may be recycled.

The invention may be executed in any suitable type of apparatus and the process may be carried out in a batch-wise, intermittent or continuous manner, although a continuous process is preferred.

The separation of the products of reaction from each other may be accomplished by processes well known in the art, e.g. distillation.

Referring to FIG. 1, 10 represents a static-bed reactor containing an absorptive catalyst. Static-beg reactor 10 is connected to coiled preheating section 12 and both reactor 10 and preheating section 12 are positioned inside electric furnace 14. Hydrogen sulfide gas is fed in through line 16 and the reactant mixture of benzene and dihalobenzene through line 18. The mixture of hydrogen sulfide gas, benzene and dihalobenzene is vaporized and preheated in section 12 at temperatures in the range of from about 300° C. to about 600° C. The gas mixture is then passed through reactor 10 where temperatures of from 400° C. to about 900° C. are maintained, and product gases leaving through line 20 are condensed to provide the desired mono-halothiophenol and thiophenol. Non-condensible by-products can be passed through a caustic scrubber (not shown).

The following examples serve to illustrate the invention and its advantages.

EXAMPLES 1-3

A static-bed reactor as illustrated in FIG. 1 was employed in the examples. The reactor 10 consisted of quartz glass 1 inch in diameter and 13 inches long and was attached to a coiled preheating section 12, consisting of ¼ inch diameter quartz tubing, 36 inches long.

The reactor 10 was filled with coal charcoal, about 100 ml., (about 1000 m$^2$/gm) and heated to a specific temperature; the preheater temperature was also set at a specific temperature. Benzene and para-dichlorobenzene were fed into the preheater at a set rate, and hydrogen sulfide was fed at a set rate. The reactants were vaporized and heated in the preheater prior to entering the reactor 10.

The gaseous products were quenched in a water cooled condenser and the products identified by comparing gas-liquid chromatography retention times with those of authentic samples of thiophenol, benzene, chlorobenzene, para-dichlorobenzene (PDB), para-chlorothiophenol (PCT), and phenyl sulfide.

The following are the results of three (3) separate runs:

| | Parameters | EXAMPLES | | |
|---|---|---|---|---|
| | | 1 | 2 | 3 |
| A. | Mole Ratio of Benzene:PDB in reactant mixture | 2:1 | 2:1 | 2:1 |
| B. | Flow Rate of Reactant mixture (Benzene plus PDB) | | | |
| | 1. ml/hr | 12 | 17 | 17 |
| | 2. moles/hr | 0.134 | 0.19 | 0.19 |
| C. | H$_2$S Flow Rate | | | |
| | 1. ml/hr | 8000 | 12000 | 12000 |
| | 2. mole/hr | 0.357 | 0.536 | 0.536 |
| D. | Ratio C.2 to B.2 | 2.7:1 | 2.8:1 | 2.8:1 |
| E. | Reaction Temperature (°C.) | 500 | 600 | 600 |
| F. | Preheater Temperature (°C.) | 400 | 400 | 400 |
| G. | Residence Time In reactor (sec.) | 12 | 9 | 9 |
| H. | Products (Mole %) | | | |
| | 1. Benzene | 0.2 | 54 | 54.1 |
| | 2. Chlorobenzene | <0.1 | — | — |
| | 3. Thiophenol | 61.6 | 7.0 | 10.8 |
| | 4. PDB | 24.3 | 30.2 | 28.4 |

-continued

| Parameters | EXAMPLES | | |
|---|---|---|---|
| | 1 | 2 | 3 |
| 5. PCT | 0.0 | 7.5 | 5.5 |
| 6. Phenyl Sulfide | 4.5 | — | — |
| 7. Others | 4 | 1.3 | 1.1 |

COMPARATIVE EXAMPLE 1

A static-bed reactor as illustrated in FIG. 1 was employed in this example. The reactor 10 consisted of quartz glass 1 inch in diameter and 13 inches long and was attached to a coiled preheating section 12, consisting of ¼ inch diameter quartz tubing, 36 inches long.

The reactor 10 was filled with coal charcoal and heated to 600° C.; the preheater temperature was set at 400° C. Benzene was fed into the preheater at a rate of addition of 0.15 moles per hour and hydrogen sulfide was fed at a rate of 0.28 moles per hour. The reactants were vaporized and heated in the preheater prior to entering the reactor 10.

The gaseous products were quenched in a water cooled condenser and the products identified by comparing gas-liquid chromatography retention times with those of authentic samples of thiophenol and benzene. The liquid condensate contained 3 percent by weight thiophenol and 97 percent by weight unreacted benzene.

This example was taken from U.S. application Ser. No. 802,682, corresponding to Belgian Pat. No. 867,645.

COMPARATIVE EXAMPLES 2 AND 3

Tests were performed in the same manner as Examples 1 through 3, except that toluene was substituted for benzene. The following is a summary of those results:

TABLE II

| | | Comparative Examples | |
|---|---|---|---|
| Parameters | | 2 | 3 |
| A. | Mole Ratio of Toluene:PDB in Reactant | 2:1 | 2:1 |
| B. | Mixture Flow Rate Of Reactant Mixture (Toluene plus PDB) | | |
| | 1. ml/hr | 17 | 17 |
| | 2. mole/hr | 0.17 | 0.17 |
| C. | H₂S Flow Rate | | |
| | 1. ml/hr | 12000 | 12000 |
| | 2. mole/hr | 0.536 | 0.536 |
| D. | Ratio to C.2 to B.2 | 3.2:1 | 3.2:1 |
| E. | Reaction Temperature (°C.) | 550 | 600 |
| F. | Preheater Temperature (°C.) | | |
| G. | Residence Time in Reactor (sec.) | 10 | 10 |
| H. | Products (Mole %) | | |
| | 1. Toluene | 66.6 | 75.2 |
| | 2. Chlorobenzene | 0 | 0 |
| | 3. Thiophenol | trace | trace |
| | 4. PDB | 30.4 | 19.5 |
| | 5. PCT | 3.0 | 1.0 |

What is claimed is:

1. A process for the production of mono-halothiophenol and thiophenol comprising reacting a reactant mixture of benzene and dihalobenzene with hydrogen sulfide in the presence of an absorptive catalyst having a surface area of from about 1 to about 1,000 square meters per gram and selected from the group consisting of:
   activated carbon,
   petroleum coke,
   charcoal,
   calcined petroleum coke,
   alumina,
   clay,
   silica gel, and
   molecular sieves.

2. The process of claim 1, wherein the dihalobenzene is para-dichlorobenzene and the monohalothiophenol produced is para-chlorothiophenol.

3. The method of claim 1, wherein the reacting step is carried out at a temperature of about 400° C. to about 900° C.

4. The process of claim 1, wherein the reacting step is carried out at a temperature of about 400° C. to about 600° C.

5. The process of claim 1, wherein the catalyst is charcoal.

6. The process of claim 1, wherein the catalyst is calcined petroleum coke.

7. The process of claim 1, wherein the catalyst is activated carbon.

8. The process of claim 1, wherein at least part of the catalyst is impregnated with a co-catalyst which is a transition metal sulfide.

9. The process of claim 1, wherein the mole ratio of hydrogen sulfide to the reactant mixture is at least about 1:1.

10. The process of claim 9, wherein the mole ratio of hydrogen sulfide to reactant mixture is no greater than 10:1.

11. In a process for producing thiophenol by reacting benzene with hydrogen sulfide in the presence of an absorptive catalyst, the improvement comprising increasing the yield of thiophenol by reacting in the presence of a yield increasing amount of dihalobenzene.

12. The process of claim 11, wherein the dihalobenzene is para-dichlorobenzene.

13. The process of claim 11, wherein the yield increasing amount of dihalobenzene is sufficient to produce a reactant mixture containing a mole ratio of benzene to dihalobenzene of from about 0.5:1 to about 3:1.

14. The process of claim 11, wherein the mole ratio of hydrogen sulfide to benzene plus dihalobenzene is at least about 1:1.

15. The process of claim 14, wherein the mole ratio of hydrogen sulfide to benzene plus dihalobenzene is no greater than 10:1.

16. The process of claim 8, wherein the transition metal sulfide is selected from the group consisting of zinc sulfide and cobalt sulfide.

* * * * *